US00PP26178P3

(12) United States Plant Patent
Conev et al.

(10) Patent No.: US PP26,178 P3
(45) Date of Patent: Dec. 1, 2015

(54) DWARF GRAPEVINE 'VDG004'

(50) Latin Name: *Vitis vinifera*
Varietal Denomination: VDG004

(71) Applicant: Vineland Research and Innovations Centre Inc., Vineland Station (CA)

(72) Inventors: Rumen Conev, St. Catharines (CA); Daryl Somers, Fenwick (CA)

(73) Assignee: Vineland Research and Innovations Centre Inc., Vineland Station (CA)

( * ) Notice: Subject to any disclaimer, the term of this patent is extended or adjusted under 35 U.S.C. 154(b) by 64 days.

(21) Appl. No.: 13/999,595

(22) Filed: Mar. 12, 2014

(65) Prior Publication Data

US 2014/0366232 P1 Dec. 11, 2014

(30) Foreign Application Priority Data

Jun. 6, 2013 (CA) ..... 13-8055

(51) Int. Cl.
*A01H 5/00* (2006.01)
*A01H 5/08* (2006.01)

(52) U.S. Cl.
USPC ..... Plt./205
CPC ..... *A01H 5/0812* (2013.01)

(58) Field of Classification Search
USPC ..... Plt./205
See application file for complete search history.

(56) References Cited

PUBLICATIONS

PLUTO Plant Variety Database Jul. 9, 2015.*

* cited by examiner

*Primary Examiner* — Annette Para

(57) ABSTRACT

The invention is a new and distinct ornamental dwarf grapevine variety denominated 'VDG004'. The new grapevine carries the REN1 gene for resistance to powdery mildew and is characterized by light green leaves, no visible hair on the young leaves, not having prominent lobes on mature leaf, having smooth leaf surface, having greenish internodes with distinctive anthocyanin accumulation on the nodes, and having small light purple berries.

7 Drawing Sheets

Latin name of the genus and species of the plant claimed: *Vitis vinifera.*

Variety denomination: 'VDG004'.

BACKGROUND OF THE INVENTION

The new and distinct dwarf ornamental grapevine described and claimed herein originated from a cross between 'Pixie'™ and unknown *Vitis vinifera* male parent, the male parent having introgressed therein a REN1 gene for powdery mildew resistance originating from 'Kishmish vatkana'.

The female parent 'Pixie'™ is a natural dwarf ornamental grapevine (*Vitis vinifera*) derived from periclinal L1/L2 chimera 'Pinot Meunier' with dark purple berry skin. 'Pixie'™ is the only known naturally dwarf grapevine in the public domain.

The pollen parent is an unknown *Vitis vinifera* line having a REN1 gene for powdery mildew resistance introgressed therein. The REN1 gene originates from 'Kishmish vatkana', an old *Vitis vinifera* variety from Uzbekistan with light purple berry skin. 'Kishmish vatkana' carries the REN1 gene for powdery mildew resistance.

The present variety of dwarf grapevine was first produced by controlled hybridization. The original cross was done at Vineland Research and Innovations Centre, Vineland Station, Ontario, Canada on Nov. 22, 2010.

'VDG004' was first successfully asexually propagated by single node softwood cuttings at the Vineland Research and Innovations Centre, Vineland Station, Ontario, Canada on Jun. 8, 2012. It is being maintained on its own roots in a container in a Canadian Food Inspection Agency certified greenhouse facility at Vineland Research and Innovation Centre, Vineland Station, Ontario, Canada.

SUMMARY OF THE INVENTION

The new grapevine 'VDG004' has the following major distinguishing characteristics. 'VDG004' carries the REN1 gene for resistance to powdery mildew and has light green leaves, has no visible hair on the young leaves, does not have prominent lobes on mature leaf, has smooth leaf surface, has greenish internodes with distinctive anthocyanin accumulation on the nodes, and has small light purple berries.

In contrast, the parent plant 'Pixie'™ does not carry the REN1 gene for resistance to powdery mildew and has very dark green leaves, has dense prominent white hairy upper surface on the young leaves, has a 3 to 5 lobe leaf structure, has a prominent blistery texture of mature leaf, has green internodes and nodes, and has dark purple medium size berries.

The characteristics most useful in distinguishing 'VDG004' from 'Pixie'™ are prostrate hairs on tip; young leaf: prostrate hairs between main veins on lower side of blade; mature leaf: blistering of upper side of blade; mature leaf: number of lobes; mature leaf: depth of upper lateral sinuses; bunch: density; berry size; berry: color of skin (without bloom); and berry: formation of seeds.

BRIEF DESCRIPTION OF THE DRAWING

The accompanying photographic illustration illustrates in full color 'VDG004'. The colors are as nearly true as reasonably possible in color representation of this type. Colors in the photographs may differ from the color values cited in the detailed botanical description below, which accurately describes the colors of the new dwarf grapevine.

DETAILED BOTANICAL DESCRIPTION OF THE INVENTION

Figure 1:
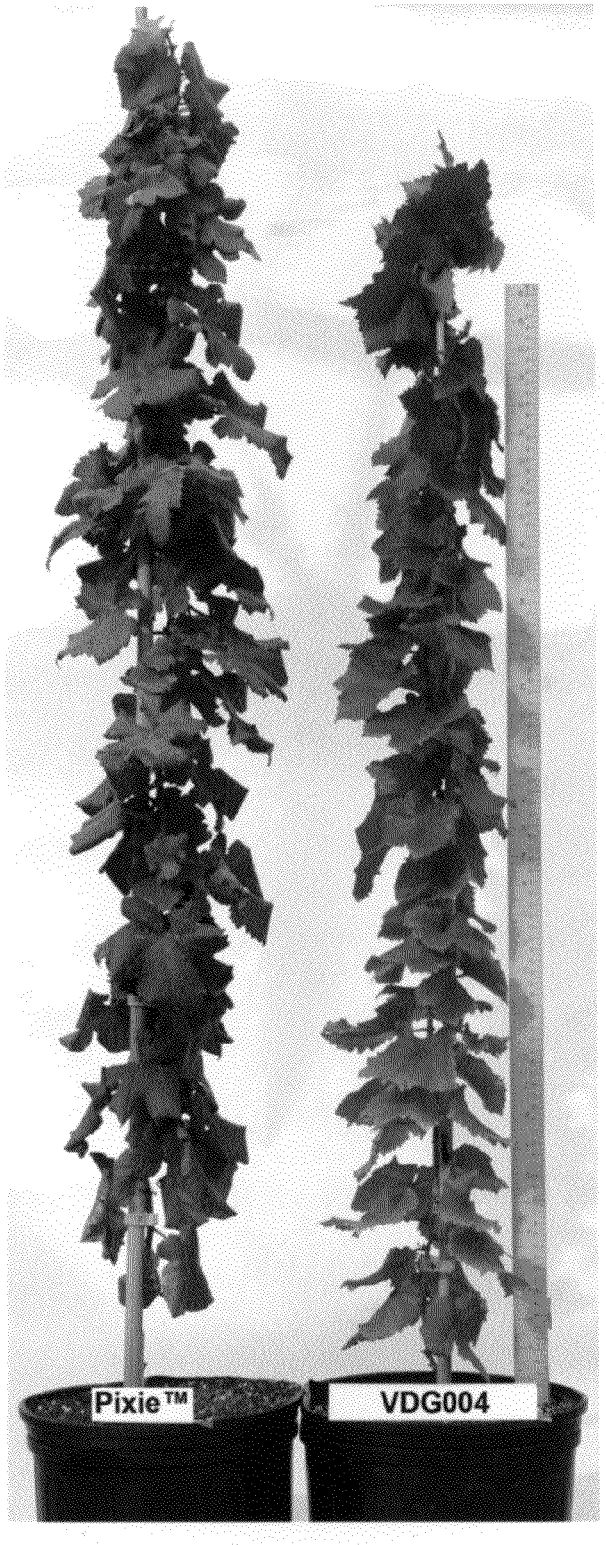
FIG. 1 shows vigor and foliage color of 'VDG004', in comparison to the female parent 'Pixie'™.
Figure 2:
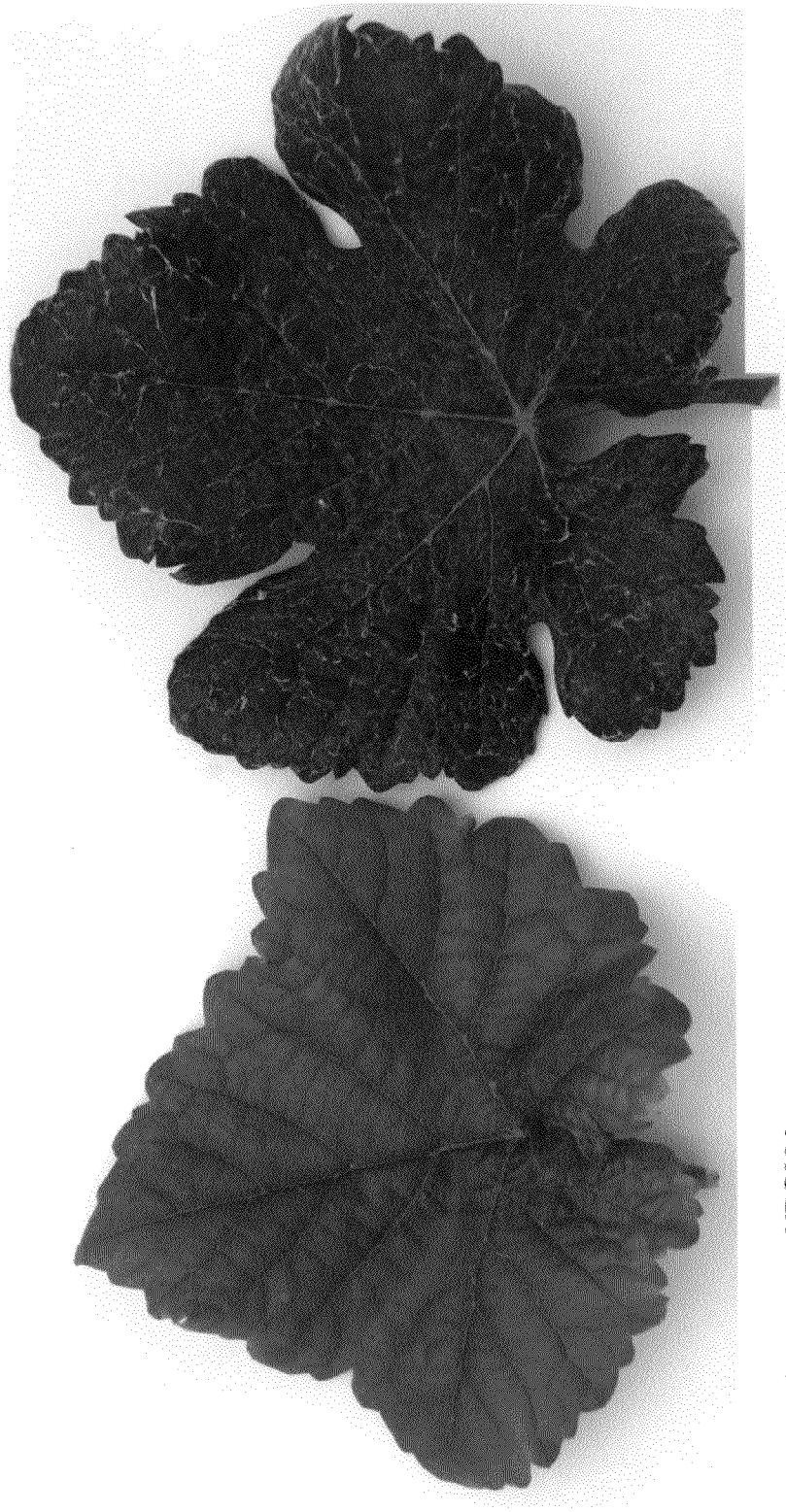
FIG. 2 shows upper side of mature leaf blades of 'VDG004', in comparison to the female parent 'Pixie'™.
Figure 3:
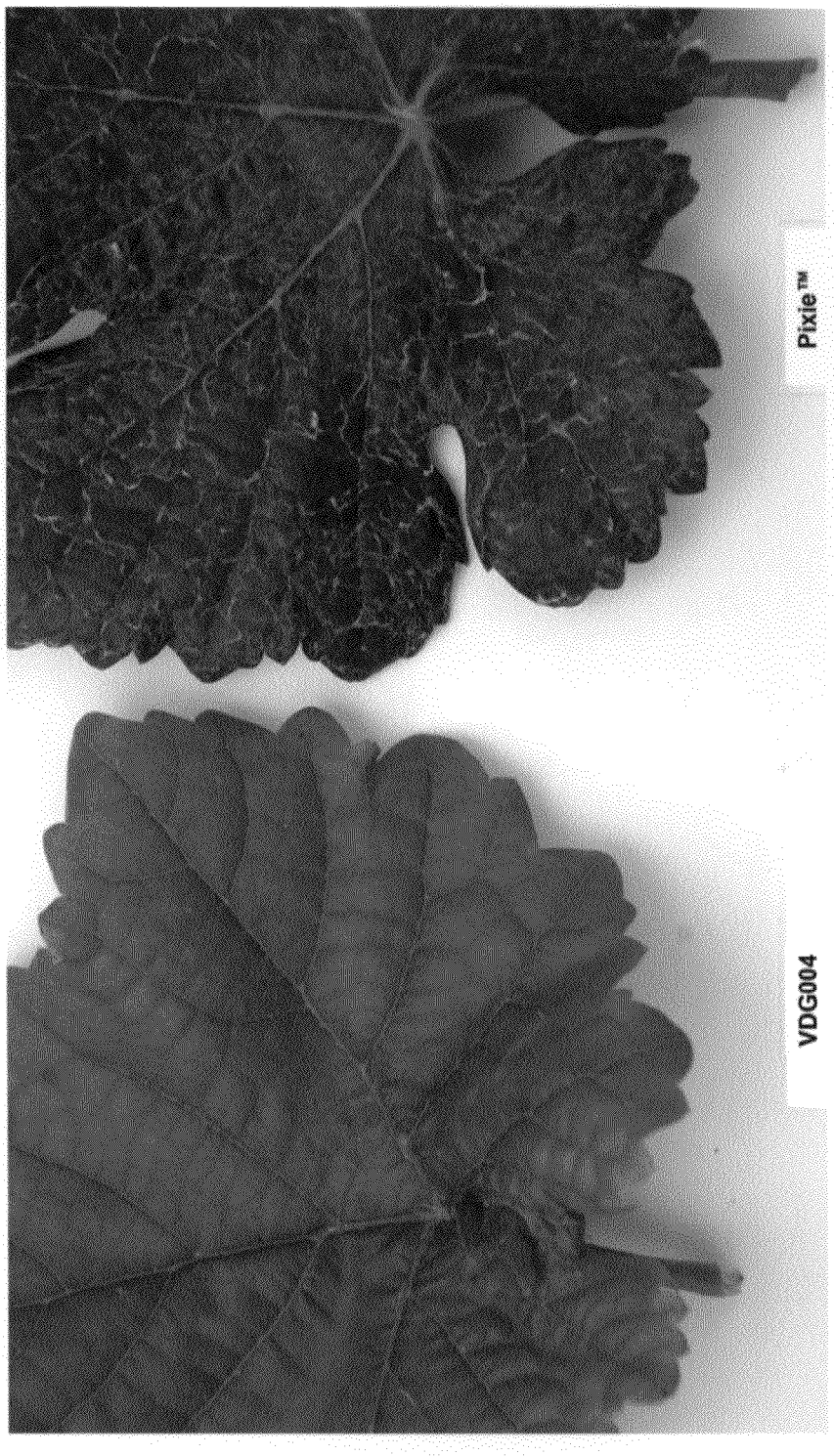
FIG. 3 shows a magnified view of upper side of mature leaf blade of 'VDG004', in comparison to the female parent 'Pixie'™.
Figure 4:
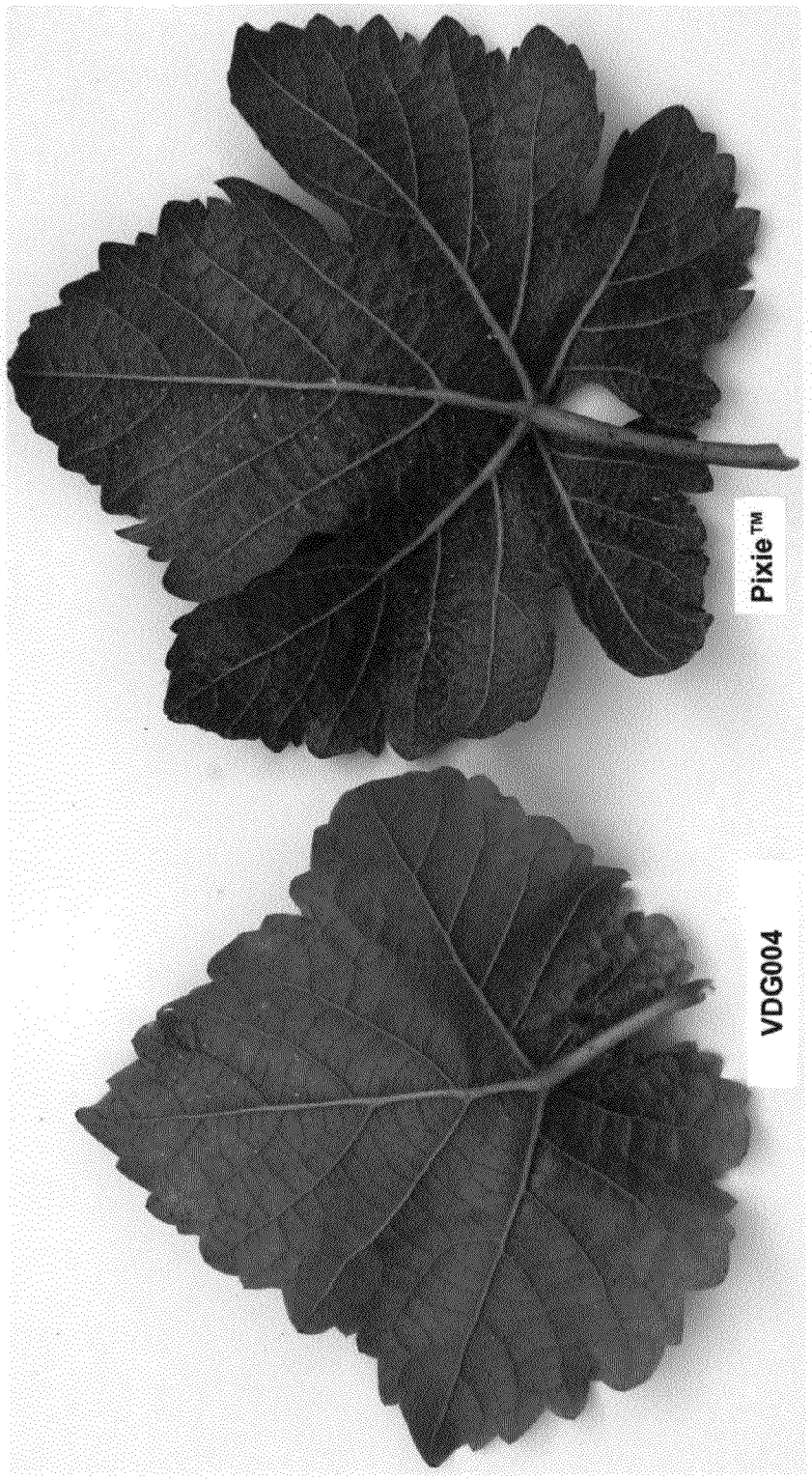
FIG. 4 shows lower side of mature leaf blade of 'VDG004', in comparison to the female parent 'Pixie'™.
Figure 5:
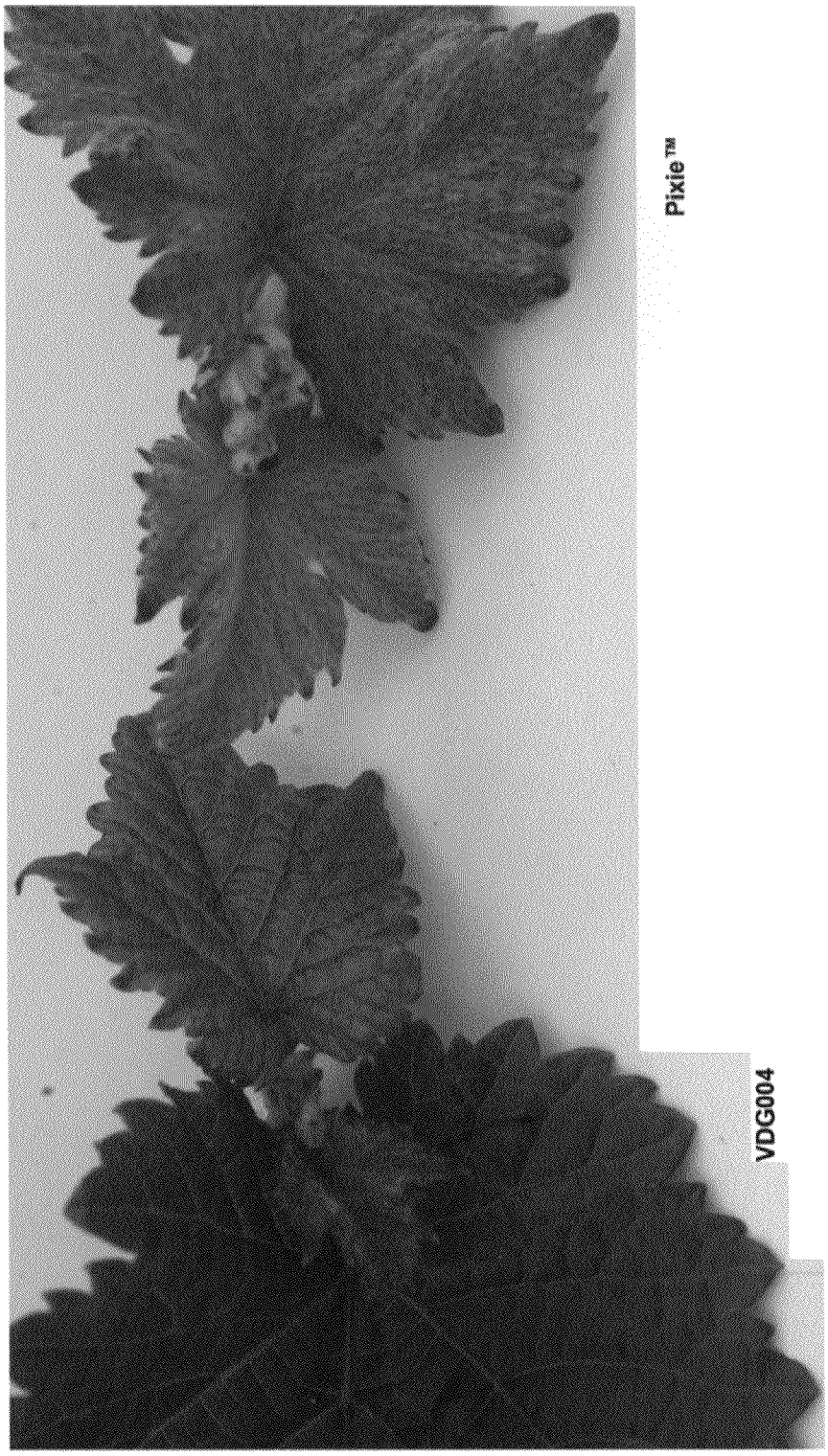
FIG. 5 shows upper side of young shoot of 'VDG004', in comparison to the female parent 'Pixie'™.
Figure 6:
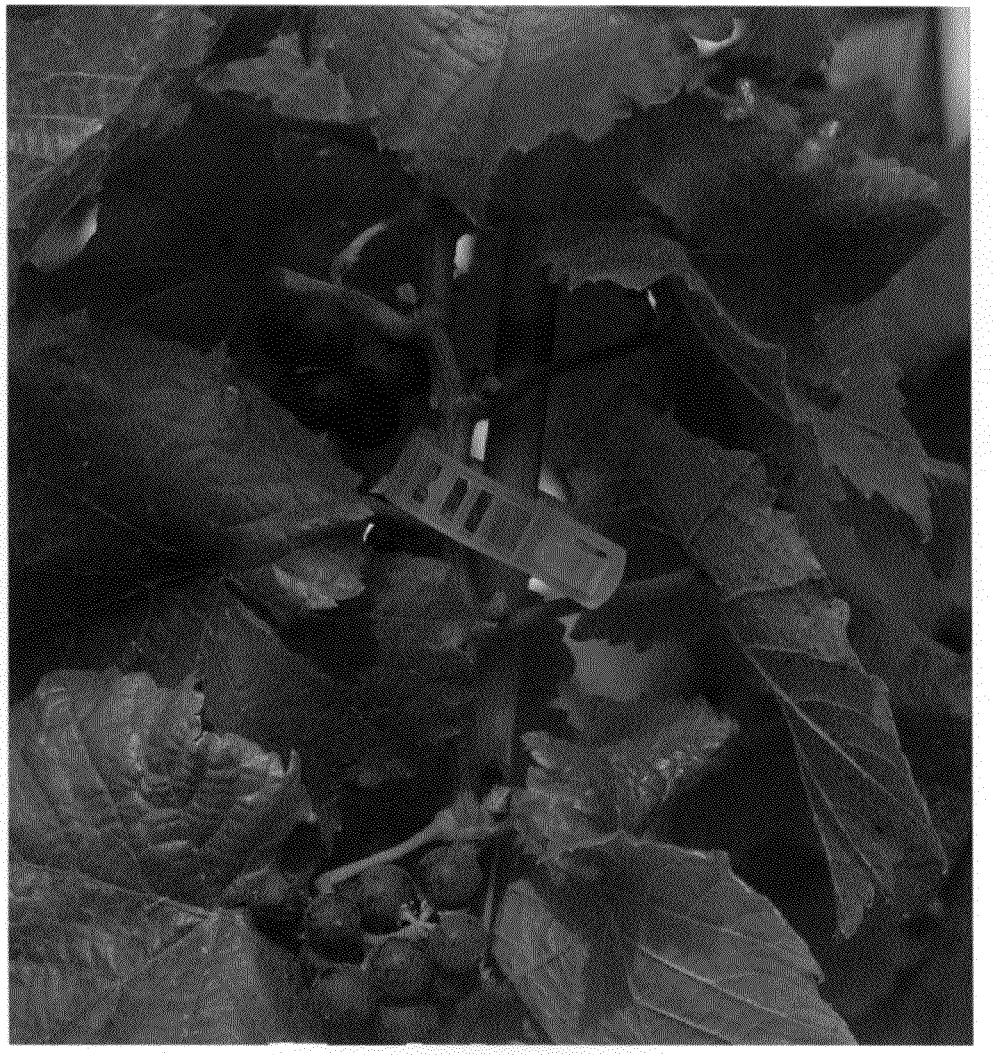
FIG. 6 shows fruiting habit of 'VDG004'.
Figure 7:
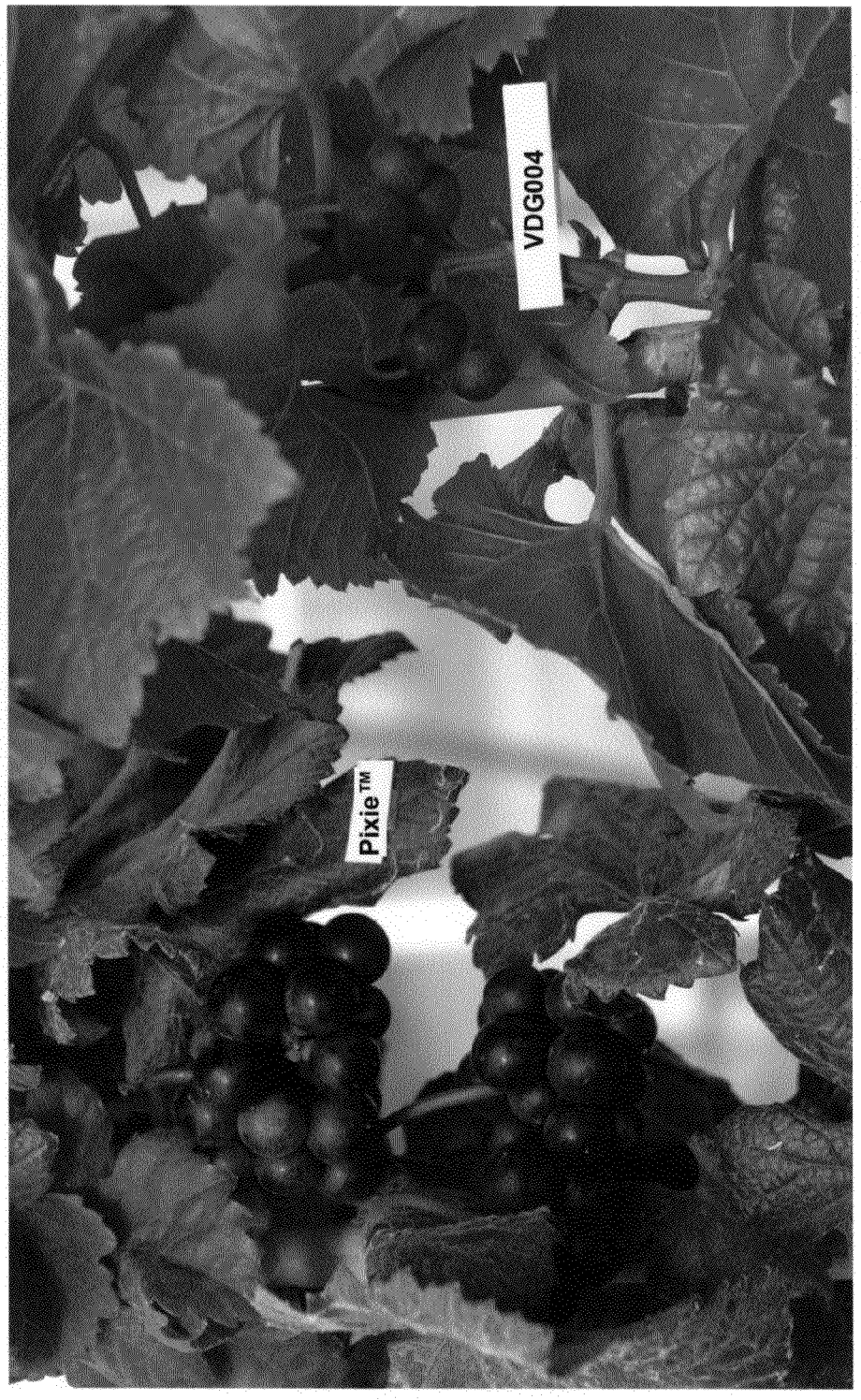
FIG. 7 shows grape bunch size and density and berry color, size and shape of 'VDG004', in comparison to the female parent 'Pixie'™.

'VDG004' is a dwarf ornamental grapevine with edible fruit. 'VDG004' has inherited the undetermined growth pattern and the dwarf growth habit from the mother variety ('Pixie'™). The internodes are 10-15 mm in length (approximately 10-20 times shorter compared to standard *Vitis vinifera* cultivars).

The variety is uniform and stable. No off-types, variants or mutations have been found to date.

The R.H.S. Colour Chart of The Royal Horticultural Society has been used for colour identification of foliage, berry skin and shoot. The description is based on the observation of 10 one year old plants growing in containers on their own roots in a greenhouse facility at Vineland Research and Innovation Centre, Vineland Station, Ontario, Canada during the years 2013 and 2015.

Time of bud burst: Not available as the plants were grown in a greenhouse.

Young shoot:
- *Openness of tip*.—Closed.
- *Prostrate hairs on tip*.—Medium.
- *Anthocyanin coloration on prostrate hairs on tip*.—Absent or very weak.

Young leaf:
- *Color of upper side of blade*.—Green (137-B).
- *Prostrate hairs between main veins on lower side of blade*.—Absent or very sparse.

Shoot:
- *Color of dorsal side of internodes*.—Green (137-C).
- *Color of ventral side of internodes*.—Green (137-C).
- *Color of dorsal side of nodes*.—Green (137-C).
- *Color of ventral side of nodes*.—Green (137-C).
- *Length of tendril*.—Very short (very scarce, very short, decline fast).

Flower:
- *Sexual organs*.—Fully developed stamens and fully developed gynoecium.

Inflorescence:
- *Type*.—Hermaphrodite.
- *Date of bloom*.—Continuous.
- *Flower cap*.—5 fused, green (138-A).
- *Flowers/cluster*.—30-110.
- *Flower diameter*.—2 mm.
- *Cluster length + peduncle*.—About 4-5 cm.
- *Pistil length*.—2.2 mm.
- *Pistil color*.—Yellow green (146-B).
- *Filament length*.—2 mm.

Mature leaf:
- *Size of blade*.—Small to very small.
- *Shape of blade*.—Circular.
- *Blistering of upper side of blade*.—Medium to weak.
- *Number of lobes*.—Three.
- *Depth of upper lateral sinuses*.—Absent or very shallow.
- *Arrangement of lobes of upper lateral sinuses*.—Open.
- *Arrangement of lobes of petiole sinus*.—Strongly overlapped.
- *Length of teeth*.—Short.
- *Ratio length/width of teeth*.—Small.
- *Shape of teeth*.—Both sides convex.
- *Proportion of main veins on upper side with anthocyanin coloration*.—Low to very low.
- *Prostrate hairs between main veins on lower side of blade*.—Absent or very sparse.
- *Erect hairs on main veins on lower side of blade*.—Absent or very sparse.
- *Length of petiole compared to length of middle vein*.—Much shorter.
- *Color of upper surface*.—Green (N137-A).

Time of beginning of berry ripening: Not available as the plants were grown in a greenhouse.

Bunch:
- *Size (peduncle excluded)*.—Very small.
- *Density*.—Medium to lax.
- *Length of peduncle of primary bunch*.—Medium to short.

Berry:
- *Size*.—Very small.
- *Shape*.—Globose.
- *Color of skin (without bloom)*.—Dark red violet (N92-B).
- *Ease of detachment from pedicel*.—Difficult.
- *Thickness of skin*.—Thin.
- *Anthocyanin coloration of flesh*.—Absent or very weak.
- *Firmness of flesh*.—Soft or slightly firm.
- *Particular flavor*.—None.
- *Formation of seeds*.—None.

Woody shoot:
- *Main color*.—Orange brown (174-B).

Genotypic analysis: Genotypic lab analysis confirmed the hybrid status of 'VDG004'. It was confirmed that it carries the REN1 gene for resistance to powdery mildew, inherited from the male parent. 'VDG-004' has not been tested to determine the degree of resistance. 'VDG-004' has no particular resistance to insects. Polymerase chain reaction (PCR) was performed on template DNA extracted from 'VDG004' using microsatellite marker primers that were polymorphic between 'Pixie'™ and the male parent. The microsatellite markers confirmed that the new variety 'VDG004' is a hybrid of the parents. The REN1 gene was detected by PCR on template DNA extracted from VDG004 based on PCR primers described in Coleman C, et al. *BMC Genetics*. 2009, 10: 89.

Biometric data of 'VDG004' is compared to that of the mother variety ('Pixie'™) in Table 1.

TABLE 1

| Biometric data | 'VDG004' | 'Pixie' ™ |
|---|---|---|
| Average size of mature leaf blade, L × W, mm | 93 × 99 | 106 × 107 |
| Length of petiole/length of main vein, mm | 31/66 | 42/77 |
| Height of central stem, cm | 122 | 98 |
| Total linear growth per plant, cm | 122 | 150 |
| Total number of nodes per plant | 93 | 117 |
| Average internode size, mm | 13 | 13 |
| First bunch set at node number | 43 | 25 |
| Average peduncle length, mm | 31.4 | 40.5 |
| Average number of berries per bunch | 8.6 | 21.6 |
| Average bunch weight, g | 3.8 | 18.9 |
| Average berry weight, g | 0.4 | 0.9 |

TABLE 1-continued

| Biometric data | 'VDG004' | 'Pixie' ™ |
|---|---|---|
| Average berry size, mm | 9.1 | 12.7 |
| Average number of seeds/berry | 0.0 | 2.7 |
| Sugar content, °Bx | 19.2 | 21.3 |

The 'VDG004' variety has not been observed under all possible environmental conditions to date. Accordingly, it is possible that the phenotypic expression may vary somewhat with changes in light intensity and duration, cultural practices, and other environmental conditions.

What is claimed:

1. A new and distinct variety of dwarf ornamental grapevine substantially as herein illustrated and described.

* * * * *